United States Patent [19]
Hollingsworth et al.

[11] Patent Number: 5,851,807
[45] Date of Patent: *Dec. 22, 1998

[54] PROCESS FOR BIOLOGICAL MATERIAL CARBON-CARBON BOND FORMATION

[75] Inventors: Rawle I. Hollingsworth, Haslett, Mich.; Seunho Jung, Kuyngkido, Rep. of Korea; Carol A. Mindock, Lansing, Mich.

[73] Assignee: Board of Trustees operating Michigan State University, East Lansing, Mich.

[ * ] Notice: This patent issued on a continued prosecution application filed under 37 CFR 1.53(d), and is subject to the twenty year patent term provisions of 35 U.S.C. 154(a)(2).

[21] Appl. No.: 784,367

[22] Filed: Jan. 17, 1997

[51] Int. Cl.$^6$ ........................................................ C12P 7/64
[52] U.S. Cl. .......................... 435/311; 435/135; 435/170; 435/244
[58] Field of Search ..................... 435/134, 135, 435/170, 244

[56] References Cited

PUBLICATIONS

Jung et al., J. Lipid Res. (1994), 35(6), 1057–65.
Klein et al., Biochem J 183 (3). 1979. 691–700.
Jung, S., et al., J. Biol. Chem. 268:2828–2834 (1993).
Jung, S. and R.I. Hollingsworth, J. Lipid Res. 35:1932–1945 (1994).
Jung, S. and R.I. Hollingsworth, J. Theor. Biol. 172:121–126 (1995).
Berube, L.R. and R.I. Hollingsworth, Biochemistry 34:12005–12011 (1995).
Sinensky, M., Proc. Nat. Acad. Sci. USA 71:522–525 (1974).
Ebil, H., in Membrane Fluidity in Bio. (Aloia, R.C., Ed.) pp. 217–236, Acad. Press, NY (1983).
Zeikus et al, Applied Environmental Micro. 53:57–64 (1987).
Glasoe, P.K., et al., J. Phys. Chem. 64:188–190 (1960).
Canale–Parola, E., Bacteriol. Rev. 34:82–97 (1970).
Doering, W. V.E., et al., J. Amer. Chem. Soc. 74:3000–3001 (1952).
Greene, F.D., et al., J. Org. Chem. 32:875–882 (1967).
Walborsky, H.M., et al., J. Org. Chem. 42:940–946 (1976).
Bobrik, M.A., et al., J. Amer. Chem. Soc. 96:285–287 (1974).
Que, L., et al., J. Amer. Chem. Soc. 96:6042–6048 (1974).
Que, L., et al., J. Amer. Chem. Soc. 97:4168–4178 (1974).
Que, L., et al., J. Amer. Chem. Soc. 97:463–464 (1975).

*Primary Examiner*—Irene Marx
*Attorney, Agent, or Firm*—Ian C. McLeod

[57] ABSTRACT

A process for providing vicinal dimethyl long chain between alkyl groups of organic compounds is described. The process uses intact or disrupted cells of various species of bacteria, particularly Thermoanaerobacter sp., Sarcina sp. and Butyrivibrio sp. The process can be conducted in an aqueous reaction mixture at room temperatures.

19 Claims, 7 Drawing Sheets

R = H, alkyl or aryl

PROCESS FOR BIOLOGICAL MATERIAL CARBON-CARBON BOND FORMATION

GOVERNMENT RIGHTS

This invention was developed under U.S. Department of Energy No. DE-FG0289ER14029 and NSF Grant No. BIR 912–006 and IBM 9507189. The U.S. Government has certain rights in this invention.

BACKGROUND OF THE INVENTION (1) Field of the Invention

The present invention relates to a novel process for carbon-carbon formation using a biological material. In particular, the present invention relates to a process which enables the formation of regio and stereo specific molecules with vicinal dimethyl groups.

(2) Description of Related Art

Because of its very unfavorable energetics, the formation of carbon-carbon bonds as shown in FIG. 1 between unactivated carbon centers by the removal of hydrogen atoms from the two bonding sites and direct connection of the two centers is a process for which there are no known biological nor many laboratory precedents. In the case of alkyl chains, carrying this out with any regio- or stereospecificity is a daunting task because energetics would be expected to be the same for any methylene group along the chain. The stability of the radical formed by removal of a hydrogen atom from the unique terminal methyl groups is less than that of one formed from a methylene group and so the specific coupling of the chain termini through the terminal methyl groups is actually less likely.

Despite the high degree of difficulty of this carbon-carbon coupling process, the evidence we present in the present application indicates that it might occur naturally in the membranes of some bacteria. One such organism is the anaerobic gram positive bacterium *Sarcina ventriculi*. In a series of earlier studies (Jung, S., et al., J. Biol. Chem. 268:2828–2834 (1993); Jung, S. and R. I. Hollingsworth, J. Lipid Res. 35:1932–1945 (1994); and Jung, S. and R. I. Hollingsworth, J. Theor. Biol. 172:121–126 (1995)), it was demonstrated that this bacterium adapted to changes in environmental conditions such as temperature and pH by forming new lipids species containing $\alpha,\omega$-very long chain dicarboxylic acids of up to 36 carbons in length. Over 80% of the total membrane acyl chains can be composed of these very long bifunctional molecules. Both the relative proportions of these unusual fatty acid species and their structures suggested they might be formed by tail to tail coupling of existing regular chain fatty acids probably via the radical species formed by simple removal of a hydrogen atom from the $\omega$-1 positions of two opposing acyl chains. A vicinal dimethyl function is therefore introduced at the site of linkage. Even if the two fatty acid species are identical, the isolated fatty acids (or dimethyl ester) must have the R, R or S, S configuration at the two new stereocenters and will therefore be optically active. This has been observed (Jung, S. and R. I. Hollingsworth, J. Lipid Res. 35:1932–1945 (1994)).

There is thus a need for a carbon-carbon coupling reaction which is easy to perform and which is reliable.

OBJECTS OF THE INVENTION

It is therefore an object of the present invention to provide a method for biological coupling of aliphatic groups. Further, it is an object of the present invention to provide a method which is simple and economical. These and other objects will become increasingly apparent from the following description and the drawings.

DESCRIPTION OF PREFERRED EMBODIMENTS

Figure 1:
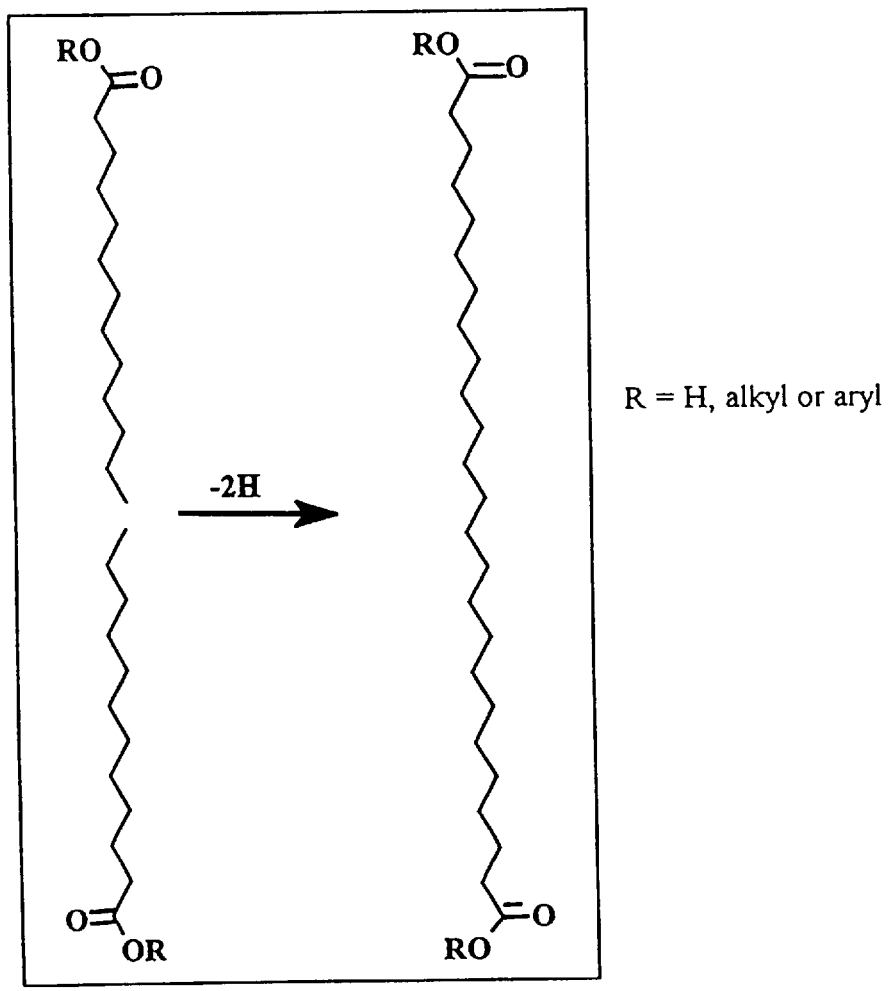
FIG. 1 is a drawing showing a schematic of a prior art chemical reaction showing joining of the tails of two opposed hydrocarbon chains to form a very long bifunctional compound.

The present invention relates to a process for formation of a long carbon chain compound which comprises: providing in an aqueous reaction mixture a cellular material of a bacterium, (preferably selected from the group consisting of the genus *Thermoanaerobacter, Sarcina and Butyrivibrio*) at least two molecules of an aliphatic group containing organic compound wherein at least one of the molecules is foreign to the bacterium and a hydrogen acceptor compound at a pH which permits formation of the long chain compound so that the molecules form a carbon-carbon bond at a beta position of each molecule and a methyl group from an alpha position of each molecule to provide the long carbon chain compound with vicinal dimethyl groups.

It has been discovered that it is possible to use these bacteria as catalytic systems to realize the hitherto unreported phenomenon of coupling of unactivated aliphatic chains between natural and unnatural hydrocarbon species.

It has been found that the enzyme system of the bacteria can be harnessed directly using membrane preparations or whole cells and utilized in synthetic organic chemistry for the stereospecific formation of carbon—carbon bonds between unactivated centers under very mild conditions. The coupling process is independent of the nature of the group at the distal ends of the hydrocarbon chains and as a result, an entire family of α,ω-bifunctional molecules can be made. The only exception is that unsaturation must be more than three carbon atoms from the terminal carbon atom of each chain. This finding has important implications for the polymer industry. The coupling activity can be used to stabilize liposomes by joining together alkyl chains at the interface between the layers of lipids or it can be used for anchoring monolayers to hydrocarbon substrates such as those formed by treating noble metal layers with alkane thiols. The present invention shows how this coupling activity can be controlled and regulated.

Devising a means whereby a foreign hydrocarbon species can react in the manner of the present invention represents a major step forward in bioorganic chemistry. It has very significant practical implications since the room temperature functionalization of an unactivated hydrocarbon chain can be achieved.

Firstly, coupling two aliphatic chains in this fashion with the liberation of two molecules of hydrogen is an energetically uphill task. To drive such a process, the chain joining is coupled to a reduction event and so this process requires an oxido-reducing system. One does not necessarily need to know what the intermediate redox system is, but it is important to know the nature of the final molecular species accepting the two hydrogen atoms. By adding this terminal hydrogen acceptor, the intermediate species that accepts the two hydrogens from the coupling is regenerated thus allowing the process to be a catalytic one.

Another element of the mechanism which has to be defined is the trigger or controlling factor regulating the activity. It seems clear that the coupling process is activated by any stimulus or condition causing an increase in fluidity or motion in the membrane lipid ensemble. Chemical studies show that the amount of chain coupling in bacteria grown at different temperatures increases with the growth temperature from essentially zero at low temperature (−30° C.) to greater than 80% at temperatures of 45° C. Studies using dynamic NMR spectroscopy (Berube, L. R. and R. I. Hollingsworth, Biochemistry 34:12005–12011 (1995)) show quite clearly that even when this high degree of coupling in the natural process occurs in response to depression of pH, the fluidity and dynamics of the aliphatic chains does not change provided they are measured at the temperature and pH at which the bacteria are grown. The coupling activity is therefore activated and also back-regulated by molecular dynamics always conserving the motional freedom of the membrane lipids within a tight range. This dynamic regulation is an important feature of the membranes of living systems and has been termed "homeoviscous adaptation" (Sinensky, M., Proc. Nat. Acad. Sci. USA 71:522–525 (1974)).

Since this coupling reaction seems to be a general response to a perturbation of membrane dynamics, a broad spectrum of perturbations trigger it. One parameter that affects the expression of this catalytic activity is pH. This catalytic activity is buried in the inner core of the membrane but it should, however, be sensitive to pH since the state of ionization of the membrane lipid head groups also helps determine the closeness of their packing (Eibl, H., in Membrane Fluidity in Biology (Aloia, R. C., Ed.) pp 217–236, Academic Press, New York (1983)). The headgroup packing will, in turn, influence the order and dynamic state of lipid aliphatic chains. PH at either extreme can be used to activate and control the reaction.

Using the present invention, foreign fatty acids, added exogenously, are joined by this stereospecific molecular machinery to form hybrid (chimeric) very long bifunctional lipid species. This is accomplished using intact cells as well as a preparation of lysed cells. The coupling process is independent of the origin of the fatty acid species and is independent of the functionality at the other end of the aliphatic chain, since it works with free acids as well as a variety of phospholipids in which the polar end contains a very forward range of functionalities. Thus, the coupling process can be used for the cell free coupling of a wide range of hydrocarbon species containing a wide variety of polar functional groups at one end.

The molecular species that can be coupled are any hydrocarbon species. These may be unsubstituted or bear any polar group at one end. These include alcohols, esters, amides, amines, glycosides, phosphate esters, sulfate esters, sulfonate esters, phosphonate esters or any polar grouping attached to a hydrocarbon chain long enough to form a micelle, monolayer, bilayer or some such aggregate. Species can be coupled to each other or to a different species to form homo or heterodimers respectively.

The coupling process involves the release of two reducing equivalents (hydrogen atoms) which should be transferred to some co-factor such as NADP or NAD via ferredoxin as an electron carrier. These reduced cofactors can then be recycled by transferring the hydrogen atoms to a ketone or aldehyde by coupling the process to the enzymatic reduction of these species to alcohols. The native bacterial cofactors were used and a variety of ketones and aldehydes were employed as terminal acceptors for the reducing equivalents with cell membranes.

The bacterium is preferably any member of the genus *Thermoanaerobacter, Sarcina or Butyrivibrio* or any related organism that is known to form very long α, ω-bifunctional fatty acids by coupling of existing regular monofunctional fatty acids. A preferred *Sarcina ventriculi* is *Sarcina ventriculi* deposited on Nov. 26, 1996 with the American Type Culture Collection as ATCC 55887. The address is 10801 University Blvd., Manassas, Va. 20110-2209. This strain is also known as ATCC 29068. *Sarcina ventriculi* JK as described by Zeikus et al, Applied Environmental Microbiology 53: 57–64 (1987) can also be used.

The coupling process can be carried out in aqueous buffer at any pH value between 3 and 10. The coupling process can be carried out in mixed aqueous/organic systems in which the organic component can be an alcohol, aldehyde or ketone.

EXAMPLE 1

Figure 3:
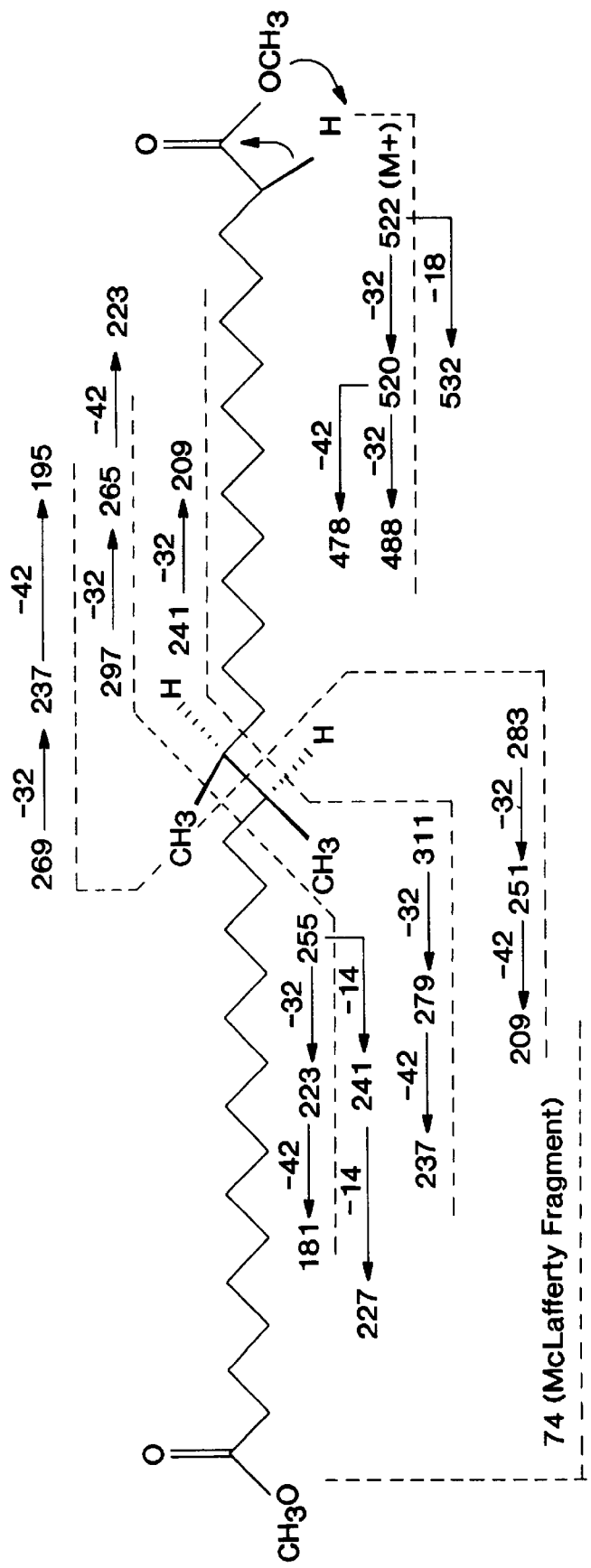
FIGS. 3 and 3A are a molecular diagram and a graph showing the electron mass spectrum of the product formed in Example 1. Only two of the four possible isomers formed in FIG. 2 are actually optically active. These are the R,R and S,S molecules. The other two are internally compensated or meso- and are thus optically inactive. An equal (racemic) mixture of the two optically active products (as will be formed in a non-selective process) are also optically inactive. A stereospecific chain-connection can, therefore, be easily identified by measuring the optical activity of the products.
Figure 3A:
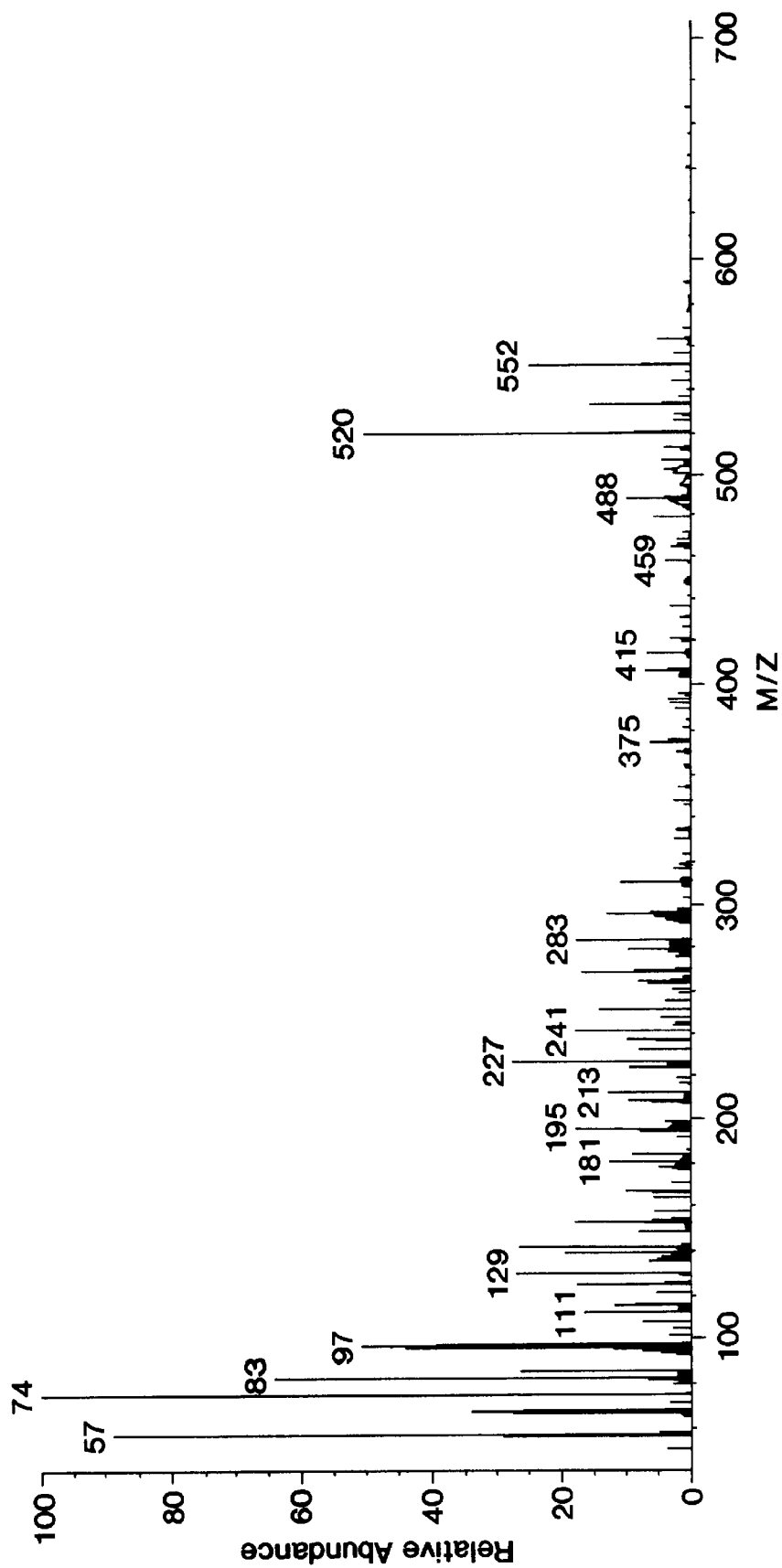

*Sarcina ventriculi* JK cells (200 ml) were cultured anaerobically in the absence of the exogenous fatty acid at 37° C. and pH 7. They were then harvested anaerobically by centrifugation, resuspended in 2 ml of oxygen free medium, lysed by French press under anaerobic conditions and heptadecanoic acid (1 mg) as an exogenous fatty acid, and methyl ethyl ketone (0.2 ml) as a hydrogen acceptor were then added. The mixture was incubated at 450 for 3 hours and then the fatty acid composition was determined by gas chromatography/mass spectrometry after converting them to methyl ester derivatives. Gas chromatography/mass spectrometry indicated that several very long bifunctional fatty acids that were not observed in the absence of exogenously added fatty acids were formed. The structures are produced by joining the foreign fatty acid (heptadecanoic acid) to one of the naturally occurring membrane fatty acid species. The electron impact mass spectrum of one such chimeric bifunctional fatty acid (as its dimethyl ester) formed by tail to tail coupling between an exogenously added fatty acid (heptadecanoic acid) and an hexadecanoic acid residue from an S. ventriculi lipid component is shown in FIGS. 3 and 3A. Detailed discussions of the fragmentation modes for these types of molecules have been presented earlier (S. Jung, et al., J. Biol. Chem. 268 2828–2835 (1993); and S. Jung and R. Hollingsworth, J. Lipid Res. 35 1932–1945 (1994)).

EXAMPLE 2

Using whole cells, four 10 ml cultures of Sarcina ventriculi JK were grown, two were controls and two had n-heptane added. Cells were incubated at 37° C. until a dense layer of cells was seen (approximately 4–6 hours). To two of the four cultures, 0.2M anaerobic n-heptane was added. Incubation of all four cultures continued at 37° C. for 2 hours while on a roller, to allow continual mixing of the n-heptane. The cells were harvested by centrifugation.

The membrane fatty acids were released from the lipids by methanolysis with 5% HCl in methanol at 80° C. for 36 hours. The mixture was concentrated to dryness under a stream of nitrogen and the fatty acid methyl esters were extracted by partitioning between chloroform and water. The chloroform layers were filtered through cotton and blown to dryness using nitrogen.

Methyl esters were analyzed by gas chromatograph (GC) and gas chromatography-mass spectrometry (GC-MS). A 30 meter DB1 column was used in both cases. The temperature program was as follows: 160° C. initial temperature, 3° C./min. rate, 320° C. final temperature, and 20 min. final time. For GC-MS, an initial ramp from 100° C. to 160° C. at 25° C./min. was also used. Samples were taken up in 5–8 $\mu$l of $CHCl_3$ and 1 $\mu$l samples were run.

Figure 4:
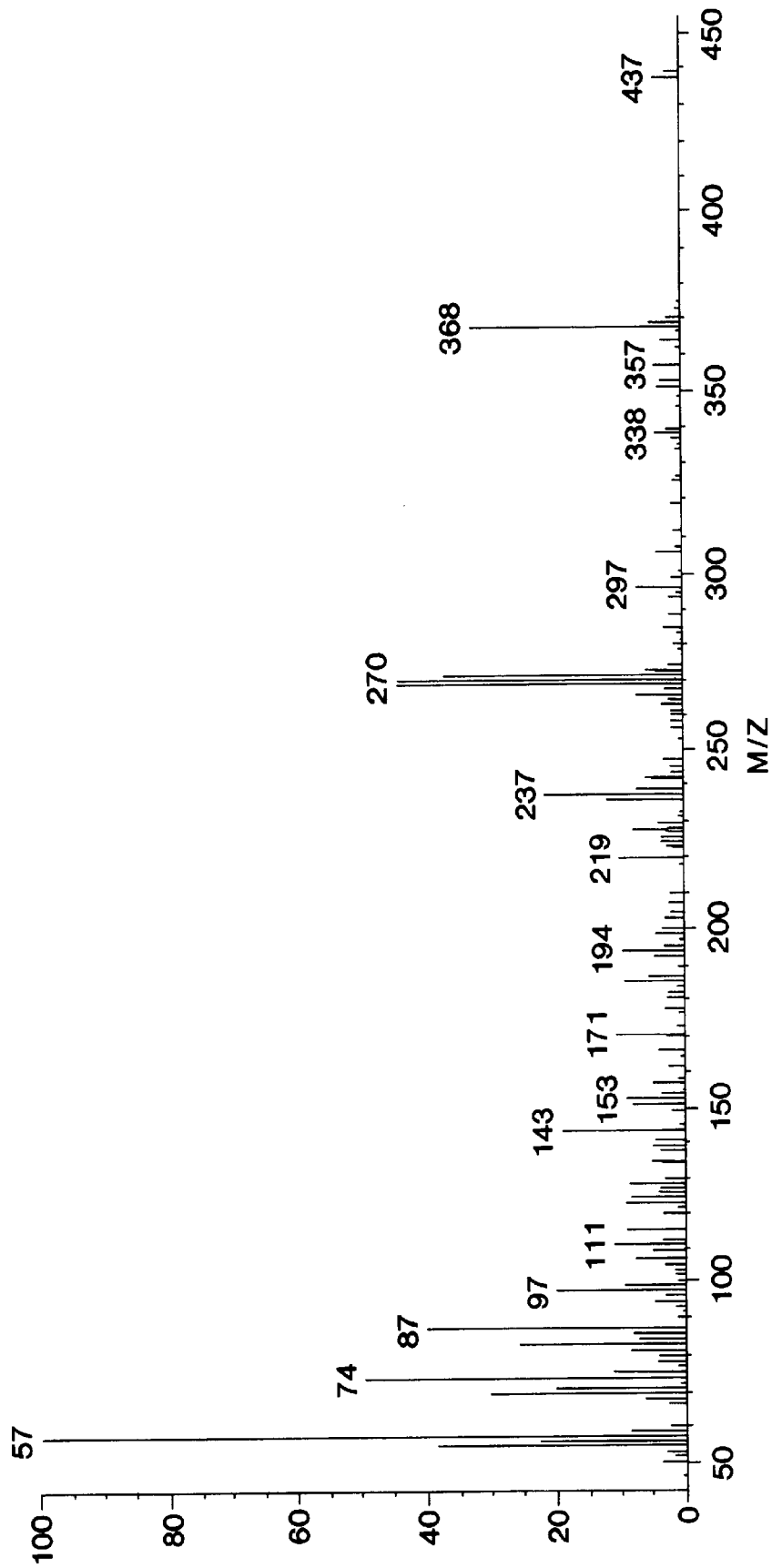
FIG. 4 is a graph showing the electron mass spectrum of a 23 carbon methyl ester produced using n-heptane in Example 2 as shown in FIG. 5. The molecular weight is 368.
Figure 5:
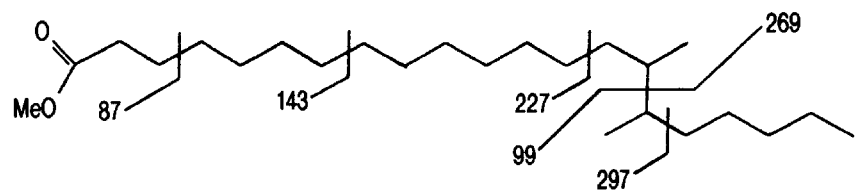
FIG. 5 is a chemical formula showing the chemical structure of the methyl ester produced.
Figure 6:
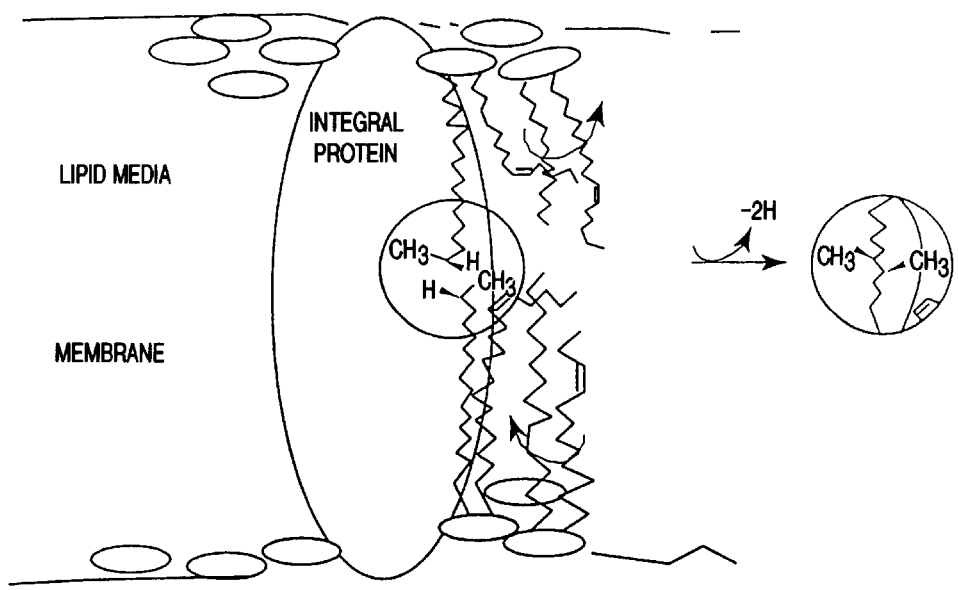
FIG. 6 is a drawing showing a conceptual model for the coupling of alkyl chains of the lipid components by an integral membrane catalytic system. Note that if the two hydrogen atoms are removed from the same side, the final product will have the methyl groups on the same side.

The major short chain lipids seen in the 37° C. control contain carbon chain lengths of 16:0, 18:0, and 18:1. No lipids containing 20–30 carbons were observed. Methyl esters containing 22 and 23 carbons were observed from those cells grown in the presence of n-heptane. The 23:0 lipid resulted from the addition of n-heptane to the 16:0 membrane lipid in the $\omega$-1 position (see FIGS. 4 and 5). Since 15:0 membrane lipids were not observed in the 37° C. control, the n-heptane was analyzed by GC and found to contain some hexane. Therefore the 22:0 methyl ester resulted from the addition of hexane to the 16:0 membrane lipid.

EXAMPLE 3

Ten milliliter cultures of Sarcina ventriculi 29068 were grown. Cells were incubated at 37° C. until a dense layer of cells was seen (approximately 12 hours). Then to two cultures, the gas headspace of two cultures were exchanged for acetylene gas, and the gas headspace of two other cultures were exchanged for propene gas. Two cultures remained as controls. Incubation of all the cultures was continued at 37° C. with shaking (speed setting of 7) for 24 hours. The headspace gases of the 37° C. controls and the acetylene cultures were removed with a syringe and transferred to nitrogen gas flushed crimp vials. These headspace gases were then analyzed by gas GC. The cells were harvested by centrifugation.

The membrane fatty acids were released from the lipids by methanolysis with 5% HCl in methanol at 80° C. for 36 hours. The mixture was concentrated to dryness under a stream of nitrogen and the fatty acid methyl esters were extracted by partitioning between chloroform and water. The chloroform layers were filtered through cotton and blown to dryness using nitrogen.

Sarcina ventriculi 29068 was unable to incorporate the acetylene or the propene into its membrane acyl chains. Thus the unsaturation must be more than three carbon atoms from the terminal carbon (i.e. more than one carbon atom away from the junction of the two (2) molecules to be joined. Analysis of the headspace gases also indicated that Sarcina ventriculi 29068 was unable to reduce acetylene to ethylene. This supports the proposed mechanism in that the cross-linking of the acyl chains occurs using a type of alcohol dehydrogenase rather than a type of nitrogenase enzyme. Studies also showed that a ketone served as a final hydrogen acceptor and was reduced to an alcohol. If a nitrogenase type of enzyme was used, the acetylene could have served as a terminal hydrogen acceptor and been reduced to ethylene, which did not occur.

EXAMPLE 4

Cells were grown under strict anaerobic conditions in liquid media as described earlier (Jung, S., et al., J. Biol. Chem. 268:2828–2834 (1993)). All cell transfers were carried out in a glove box under an oxygen free atmosphere provided by argon which was passed over heated copper to remove traces of oxygen. Cells were harvested by centrifugation at 8000 rpm in a Sorvall centrifuge equipped with a GSA rotor. For experiments that required pH control of growth conditions, bacteria were grown in a chemostat equipped with a pH probe. The chemostat was also fitted with an inlet for adding sodium hydroxide or hydrochloric acid solution via a peristaltic pump under pH feedback. Cells were cultured at 37° C. at pH 3, 7 or 9.7. The pH conditions were maintained by adding 5M sodium hydroxide for growth at pH 7 or 9.7 or hydrochloric acid for growth at pH 3. For growth of cells in 99% deuterium oxide, cells were preconditioned by culturing them in increasing concentrations of deuterium oxide until they were adapted to growth at 99%. The growth temperature was 37° C. In these experiments, the pD or pH of the growth medium was allowed to drop to ~4, conditions that normally trigger the formation of very long $\alpha,\omega$-bifunctional fatty acids. It should be noted that the measured pD is typically about 0.4 units lower than the corresponding pH value (Glasoe, P. K., et al., J. Phys. Chem. 64:188–190 (1960)).

For the cell-free coupling of free fatty acids to membrane lipids, cells (200 ml) were cultured anaerobically in the absence of exogenous fatty acid at 37° C. and a pH of 7. They were then harvested in an inert atmosphere (argon) by centrifugation and resuspended in 2 ml of oxygen free growth medium. They were lysed in a French pressure cell under anaerobic conditions and hexadecanoic acid (10 mg) as the fatty acid and ethyl ketone (10 ml) as the acid acceptor were then added. The mixture was incubated at 45° C. for 3 hours and then the fatty acids were released from the lipids by methanolysis with 5% HCl in methanol at 75° C. for 24 hours. The mixture was concentrated to dryness under a stream of nitrogen and the fatty acid methyl esters were extracted by partitioning between chloroform and water. The chloroform extract was subjected to GCMS analysis using the method described earlier (Jung, S., et al., J. Biol. Chem. 268:2828–2834 (1993)).

Cells (10 ml) were cultured at 37° C. as described above except that tert-butyl thiol (0.23 ml), and n-butane thiol (0.21 ml) was added. The reagents were added to the cultures in early log phase to the final concentrations indicated, then the temperature was shifted to 50° C., and the cells were harvested in early stationary phase (about 2 hours later). The pH was not regulated.

In a prior study, it was demonstrated that *Sarcina ventriculi* carries out tail to tail coupling of its membrane lipids in response to agents lowering the pH (Jung, S., et al., J. Biol. Chem. 268:2828–2834 (1993)). It might be argued that the coupling response might have some ionic component which is acid catalyzed. An explanation that appears to be more consistent with the profile of this response, however, is simply that lowering of pH should suppress the ionization of the phosphate groups in the membrane lipids thus reducing their electrostatic cross-linking with calcium ions thus decreasing membrane stability. Such an argument would require coupling at high pH, since then the phosphate groups would be over-ionized. The resulting electrostatic repulsion should also destabilize the membrane thus triggering the process. Observing coupling at high pH would also rule out any acid catalysis. The gas chromatography profile of fatty acid methyl esters from *Sarcina ventriculi* cells cultured at pH 9.7 shows a family of peaks with very long retention times is seen in the pH 9.7 chromatograms. This was the case for all of the other late eluting peaks in the profile. They were all readily identifiable as very long chain bifunctional species observed when these bacteria are cultured at low pH, high temperature or in the presence of organic solvents again demonstrating the universality of the response.

To further test the hypothesis that tail to tail coupling is triggered by changes in the physical state of the membrane, *Sarcina ventriculi* was cultured in $D_2O$. The stronger hydrogen bonds in $D_2O$ should slow down the lipid molecular motions, which would be equivalent to a reduction in temperature. The proportion of transmembrane lipids should differ between cells cultured in $H_2O$ versus those cultured in $D_2O$. In these experiments, the pH was allowed to drop freely as a result of acetic acid production by the bacteria (Canale-Parola, E., Bacteriol. Rev. 34:82–97 (1970)),, usually reaching a minimal pH of 4.0. A reduction in pH is known to promote the formation of long chain lipids leading to a high proportion of transmembrane lipids. If the cells are cultured in $D_2O$, however, the reduced motional dynamics in the hydrogen bonding network in the lipid headgroup and in the various solvent cages should stabilize the membrane thus off-setting the fluidizing effects of the low pH. This is exactly what was observed. A high proportion of transmembrane fatty acids is seen in the cells grown in $H_2O$. In contrast, a very small proportion is observed in the cells cultured in $D_2O$. These results are consistent with the idea that substituting $D_2O$ for $H_2O$ is equivalent to a reduction in temperature causing an increase in membrane viscosity. The cells respond by maintaining a low lever of long chain lipids. A similar kinetic effect of $D_2O$ on lipid composition has recently been reported (Hollingsworth, R. I., J. Theor. Biol. 172:121–126 (1995)). *Bacillus subtilis* was grown in $D_2O$ and the proportion of lipids with alkyl chain length of 16 carbons increased relative to those of 18 or 20 carbons.

EXAMPLE 5

Figure 7:
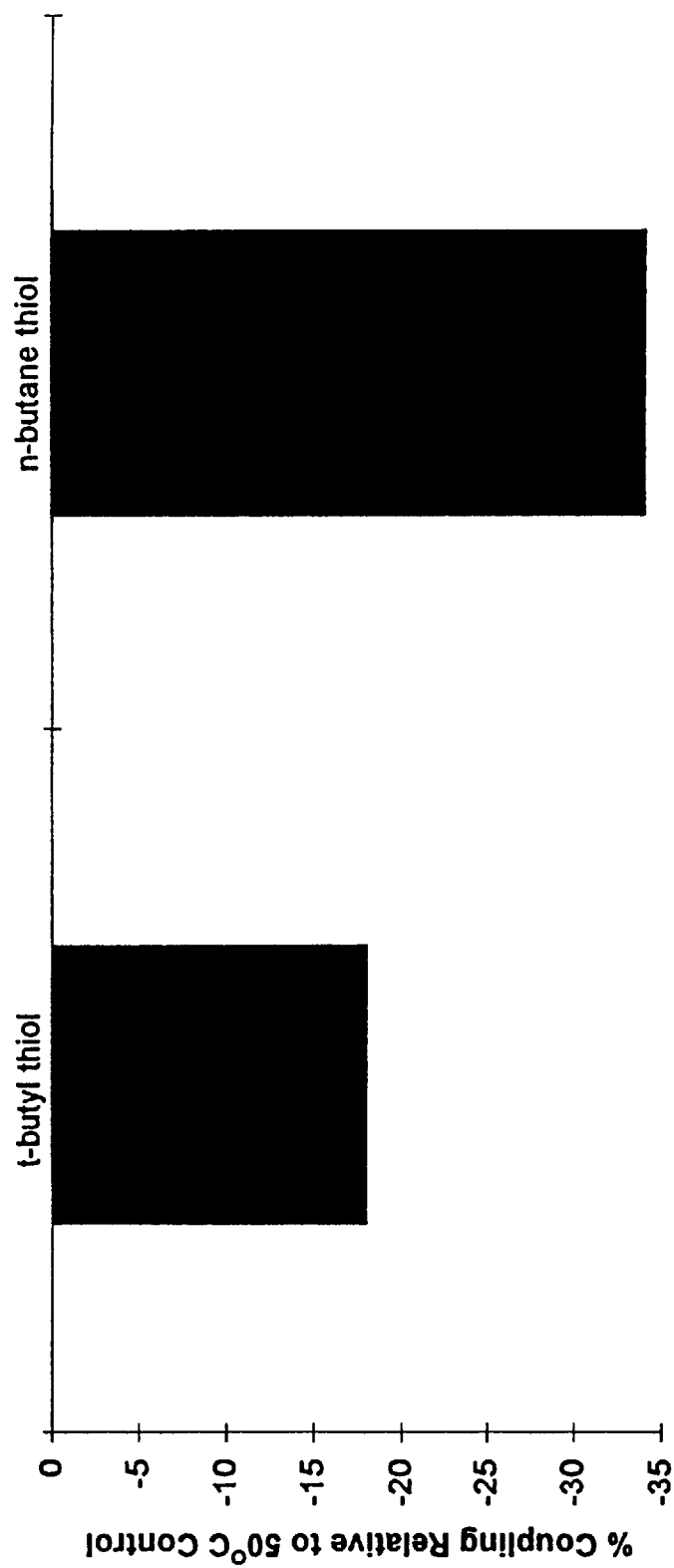
FIG. 7 shows results from radical scavenger experiments using a thiol indicating the percent of tail to tail coupling of *Sarcina ventriculi* membrane lipids normalized to the 50° C. controls. Thiols inhibit the coupling process indicating that it is radical induced since they scavenge radicals or degrade the iron sulfur systems that promote radical formation.

The coupling mechanism is temperature dependent, is triggered both by high and low pH values and is inhibited by thiols as shown in FIG. 7. The process is suppressed if cells are cultured in deuterium oxide indicating that the trigger is a kinetic factor related to motional dynamics. These results and results from NMR spectroscopy indicate that the process is regulated by membrane dynamics and occurs via a radical mechanism in which a hydrogen atom is extracted from each alkyl chain and the two alkyl radicals join to form a new carbon carbon bond. The stereospecific formation of carbon-carbon bonds between unactivated carbon centers by this system has very high potential for use in synthetic organic chemistry.

The proposed mechanism for tail to tail coupling of membrane lipids is that hydrogens are removed form the ω-1 positions of two opposing alkyl chains forming radicals which quickly combine. Since these bifunctional fatty acid species are chiral, they should not be readily accessible to radical traps or scavengers. Radicals planarize rapidly, much faster than the timescale for diffusion from the cage in which they are formed (Doering, W. v.E., et al., J. Amer. Chem. Soc. 74:3000–3001 (1952); Greene, F. D., et al., J. Org. Chem. 32:875–882 (1967); and Walborsky, H. M., et al., J. Org. Chem. 42:940–946 (1976)). This notwithstanding, it was of interest to assess the effects of radical scavengers on this system. Such experiments were important from another perspective. It was clear from previous experiments that oxygen had an adverse effect on the coupling activity. This would indicate either a radical process or the presence of an oxygen labile species such as an iron-sulfur complex. Reagents which would allow these possibilities to be tested were added to *Sarcina* cultures growing at 37° C., then the temperature was raised to 50° C. to trigger the coupling reaction. The use of a radical scavenger is a very direct way of testing whether any accessible radical species are generated in the coupling reaction. This was done using thiols, which react very rapidly with radicals, and as a result are good probes to see if, during the coupling process, any which might be generated are accessible. Two thiols, t-butyl thiol and n-butane thiol, were used and both inhibited coupling (FIG. 7). Iron-sulfur species are very sensitive to thiols (Bobrik, M. A., et al., J. Amer. Chem. Soc. 96:285–287 (1974); Que, L., et al., J. Amer. Chem. Soc. 96:6042–6048 (1974); Que, L., et al., J. Amer. Chem. Soc. 97:4168–4178 (1974); Que, L., et al., J. Amer. Chem. Soc. 97:463–464 (1975)) and this inhibition could be indicative of the presence of such a center and not the presence of an accessible radical center.

It is clear that thiols can inhibit cross-linking via another mechanism besides radical scavenging. One possibility is that they are extruding iron-sulfur centers from the necessary cofactors such as ferredoxin (Que, L., et al., J. Amer. Chem. Soc. 97:463–464 (1975)), thus breaking the electron transfer chain and stopping the recycling of the hydrogen acceptor. The involvement of iron-sulfur centers is also consistent with the oxygen lability of the coupling process.

The hydrocarbon chain coupling phenomenon of the present invention has no known precedent in the literature. The coupling conditions are mild and the regio- and stereospecificity is extremely high. It is independent of the nature of the functional groups on the distal ends of the carbon chains. The stereoselective formation of carbon-carbon bonds between unactivated centers is viewed as the last frontier in carbon-carbon bond formation.

Figure 2:
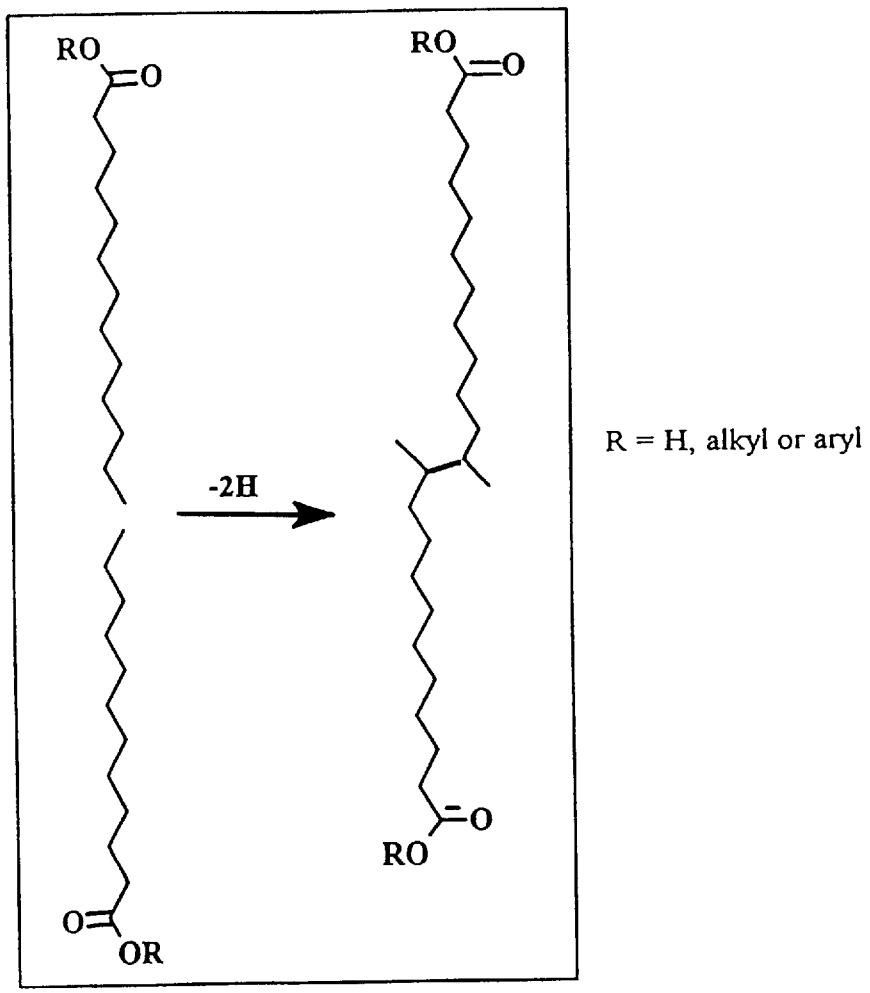
FIG. 2 is a drawing showing a chemical reaction showing joining of the tails of two opposed hydrocarbon chains at their $\omega$-1 positions to form a very long bifunctional compound with vicinal dimethyl groups according to the present invention. The points of linkage can have either the (S)-configuration or the (R)-configuration. Four isomers are thus possible (R,R); (S,S); (R,S) and (S,R).

Applications of the present invention include:

(1) The ends of long chain polar molecules can be joined to form very long chain bifunctional molecules as shown in FIG. 2. For instance dicarboxylic acids for use in the preparation of polyesters can be made this way. So can ω-hydroxy acids by the coupling of an alcohol with an acid.

(2) The coupling activity gives chiral products, therefore it can be used for this purpose.

(3) The coupling takes place only at the ω-1 position and so the coupling activity can be used for making linkages between these positions.

(4) Carbon-carbon bond formation between two sites normally requires that both sites be functionalized and activated by some chemical entity such as a halo group and a carbonyl function in the case of alkylation of an enolate or a ketone group and a magnesium halide in the case of the Wittig coupling. In this case coupling can be effected in the absence of any activating group on either molecule to be coupled.

(5) The two leaflets of membrane bilayers are held together by van der Waals forces which can be easily disrupted by temperature or by solvents. The coupling activity described can be used to attach the two leaflets together by covalent bond formation between alkyl chains from opposing leaflets.

(6) Surfaces are often covered with a hydrocarbon monolayer in the fabrication of molecular devices. The activity described here can be used to anchor such monolayers to hydrocarbon chains on the surface on which they are layered thus stabilizing them.

(7) Liposomes are hollow spherical structures made of bilayer membrane systems. They are used for a variety of functions including encapsulation of drugs, dyes, fertilizers and the like. These can be stabilized by chemically linking the two membrane leaflets together via their alkyl chains. This will make them more stable to pH, temperature, pressure, the presence of organic solvents and the like.

(8) Micelles are formed using the membrane preparation by joining chain termini.

(9) Layers of the bilayers are joined together using the membrane preparation.

(10) Extending the lengths of long chain hydrocarbons bearing a polar group at one end.

It is intended that the foregoing description be only illustrative of the present invention and that the present invention be limited only by the hereinafter appended claims.

We claim:

1. A process for formation of a long carbon chain compound which comprises;

(a) reacting in an aqueous reaction mixture in absence of whole cells at a pH between pH 3 and pH 10 (1) a cellular material of a bacterium selected from the group consisting of *Thermoanaerobacter*, *Sarcina* and *Butyrivibrio*, wherein the cellular material is a cellular membrane fragment, (2) two molecules of long chain aliphatic compound having a terminal methyl group wherein at least one of the molecules is exogenous to and foreign to the bacterium and (3) an added hydrogen acceptor compound, wherein the two molecules of (2) form a carbon-carbon bond with the cellular membrane fragment as a catalyst, at a position of each molecule adjacent to the methyl group to provide the long chain carbon compound with vicinal dimethyls adjacent to the carbon-carbon bond; and (b) separating the long chain aliphatic compound with the vicinal dimethyls from the cellular membrane material.

2. The process of claim 1 wherein the hydrogen acceptor compound is selected from the group consisting of an aldehyde and ketone which forms an alcohol during the reacting.

3. The process of claim 1 wherein the cellular membrane fragment is produced by a French press.

4. The process of claim 1 wherein wherein the two molecules of (2) are both fatty acids.

5. The process of claim 1 wherein the one of the molecules which is foreign to the bacterium is selected from the group consisting of an alcohol, an amide, a glycoside, a phosphate ester, a sulfate ester, a sulfonate ester, and a phosphonate ester.

6. The process of claim 1 wherein the molecules have a polar group as part of the long chain aliphatic group.

7. The process of claim 6 wherein the two molecules of (2) are in an assembly selected from the group consisting of a micelle, a monolayer, a bilayer and a liposome.

8. The process of claim 1 wherein the cellular membrane fragment is present in catalytic amounts.

9. The process of claim 1 wherein the cellular membrane fragment is from *Butyrivibrio* sp..

10. The process of claim 1 wherein the cellular membrane fragment is from *Sarcina* sp..

11. The process of claim 10 wherein the *Sarcina* sp. is *Sarcina ventriculi* which is deposited as ATCC 55887.

12. The process of claim 1 wherein one of the molecules of (2) is a fatty acid.

13. The process of claim 1 wherein one of the molecules of (2) is hexadecanoic acid.

14. The process of claim 1 wherein one of the molecules is hexadecanoic acid and the other of the molecules is heptadecanoic acid which heptadecanoic acid is foreign to the bacterium.

15. The process of claim 1 wherein the one of the molecules which is foreign to the bacterium is unsaturated.

16. The process of claim 1 wherein one of the molecules which is foreign to the bacterium is an unsubstituted alkane.

17. The process of claim 16 wherein the alkane is n-hexane.

18. The process of claim 1 wherein the pH is about pH 7.

19. The process of claim 1 wherein the cellular membrane fragment is from *Thermoanaerobacter* sp.

* * * * *

UNITED STATES PATENT AND TRADEMARK OFFICE
CERTIFICATE OF CORRECTION

PATENT NO. : 5,851,807
DATED : December 22, 1998
INVENTOR(S) : Rawle I. Hollingsworth, Seunho Jung and Carol A. Mindock It is certified that error appears in the above—identified patent and that said Letters Patent is hereby corrected as shown below:

Column 3, line 41, "(-30°C)" should be --(~30°C)--.

Column 4, line 61, "450" should be --45°--.

Signed and Sealed this

Twenty-eighth Day of September, 1999

Attest:

Q. TODD DICKINSON

*Attesting Officer*  *Acting Commissioner of Patents and Trademarks*